United States Patent [19]

Handt

[11] 4,405,315
[45] Sep. 20, 1983

[54] SPIKE EXCHANGER FOR CONTINUOUS AMBULATORY PERITONEAL DIALYSIS

[75] Inventor: Alan E. Handt, Zionsville, Ind.

[73] Assignee: Stephen R. Ash, Lafayette, Ind.; a part interest

[21] Appl. No.: 371,310

[22] Filed: Apr. 23, 1982

[51] Int. Cl.³ .......................... A61M 5/14; A61J 5/00
[52] U.S. Cl. ........................ 604/80; 604/29; 604/411; 222/83; 141/330
[58] Field of Search ..................... 604/27–30, 604/33, 34, 407, 408, 410–413, 406, 905, 80, 81, 246, 249, 257, 261, 262; 222/83, 89, 83.5, 129, 145; 141/330, 248; 137/318, 635; 53/469; 248/95; 285/12

[56] References Cited

U.S. PATENT DOCUMENTS 3,413,097 11/1968 Jungner .......................... 141/248 X
3,853,158 12/1974 Whitty .......................... 141/330 X

FOREIGN PATENT DOCUMENTS

WO80/02706 12/1980 PCT Int'l Appl. ................... 604/29

OTHER PUBLICATIONS

Strosahl, et al., "Visual Impairment-Not a Contraindication for Continuous Ambulatory Peritoneal Dialysis", *Dialysis and Transplantation,* vol. 10, No. 5, May 1981, pp. 371, 372, 374, 375, 378.

*Primary Examiner*—Richard J. Apley
*Assistant Examiner*—Michelle Lester
*Attorney, Agent, or Firm*—Woodard, Weikart, Emhardt & Naughton

[57] ABSTRACT

A spike exchanger to move a spike from one peritoneal dialysis bag to another. A pair of peritoneal dialysis bags are mounted to a base having clamps for releasably closing the tubular ports of each bag. A patient connectable tube with a spike shaped end is removably mounted to a bar slidably mounted on the base and guided by means of a slot and roller combination to the tubular port of either bag. Three embodiments of the slot roller mechanism guide the spike shaped end to the tubular ports.

14 Claims, 10 Drawing Figures

SPIKE EXCHANGER FOR CONTINUOUS AMBULATORY PERITONEAL DIALYSIS

BACKGROUND OF THE INVENTION

This invention is in the field of medical devices and more specifically those devices provided to exchange a tubular spike from one bag of fluid to an adjacent bag of fluid. The device disclosed herein is particularly advantageous in changing a tubular spike from one peritoneal dialysis bag into an adjacent peritoneal dialysis bag while ensuring the connection remains sterile. Peritoneal dialysis takes advantage of the fact that the peritoneal cavity is covered by a peritoneal membrane (a thin shiny membrane covering the abdominal cavity) which can be used for transfer of body waste from the blood into the peritoneal fluid instilled into it. To perform peritoneal dialysis, a dialysis solution is placed within the abdominal cavity and left there for a period of time. During this time, molecules of waste particles from the blood diffuse across the peritoneal membrane into the fluid and the fluid is subsequently drained out and discarded with new fluid being put into the peritoneal cavity to begin the process anew.

The aforementioned process is relatively slow as compared to hemodialysis; however, with the advent of continuous peritoneal dialysis the previously described process becomes a much preferred and efficient method of treatment. In 1975, Popovich and Moncrief, described the exchange method of C.A.P.D. (continuous ambulatory peritoneal dialysis) in which two liters of fluid are placed in the abdomen and left to dwell for a period of four to eight hours. At the end of this time, the fluid is drained and two liters of new fluid is put back into the abdominal cavity. A modification of this procedure by Oreopoulos in 1977 included the use of peritoneal dialysis solution in two liter bags. The bags could then be rolled up (in the empty state) during the dwell time. These patients were amubulatory and required only one bag connection for both infusion and drainage of the fluid. C.A.P.D. has now expanded widely with over 5,000 patients in the United States now receiving this therapy for chronic renal failure. When the patient changes from the old bag to a new bag connected to the tubing inserted into the abdominal cavity, the patient must under sterile conditions remove the plastic spike from the bag that is to be discarded and sterilely place this spike into the new bag. The method now used calls for the patient to have enough strength to pull the spike out of the bag and insert it into the new bag without any deviation.

There are many advantages to C.A.P.D. For example, the patient is ambulatory, is extremely mobile and can travel virtually anyplace desired as long as the bags of fluid are taken with the patient. Further, C.A.P.D. can be performed by the patient without requiring the help of a partner. It is desirable to place a number of patients on C.A.P.D.; however, there are some limitations with the method of spike exchange now used. It has been shown that diabetics have an increased incidence of blindness and it is believed the blindness is hastened by hemodialysis. Thus, it is beneficial to place these patients on C.A.P.D. This is quite difficult because the patient cannot see well enough to make the exchanges under sterile conditions and the spike becomes contaminated resulting in the patient developing peritonitis. If a blind patient or a patient with limited muscle strength or dexterity is to be placed on C.A.P.D., a partner must be used and thus decreasing the true advantages of C.A.P.D. Therefore, it would be ideal to have a mechanism by which a person who is blind, has failing eyesight, has decreased manual dexterity or decreased strength in his hands could perform the exchange of the spike by himself. Disclosed herein is such a piece of equipment allowing the change of the tubing spike from the used bag to a new bag without contamination. The exchange can be done with minimal effort with someone who has decreased vision, blindness, decreased manual dexterity or extreme weakness of the hands.

SUMMARY OF THE INVENTION

One embodiment of the present invention is a spike exchanger for continous ambulatory peritoneal dialysis comprising a base having mounting means to releasably hold a first bag with a first port and a second bag with a second port, clamp means on the base and engageable with the first port and the second port to releasably limit fluid flow therethrough, spike holding and moving means movably mounted to the base and operable to releasably hold a spike in fluid communication with the first port and move the spike away from the first port to the second port, and guide means on the base and associated with the spike holding and moving means to guide and align the spike with the second port as the spike is moved thereto.

Another embodiment of the present invention is a medical apparatus comprising a first bag for holding liquid and including a first tubular port, a second bag for holding liquid and including a second tubular port, a frame with mounting means to releasably hold the first bag and the second bag, clamp means mounted to the frame and releasably engaged with the first tubular port and the second tubular port to control fluid flow therethrough, a patient connectable tube with a spike shaped male end in fluid communication with and fittable into the first tubular port when aligned therewith and into the second tubular port when aligned therewith, operator means movably mounted to the base and releasably holding the spike shaped male end, the operator means movable from a first position whereat the male end is in the first port to the second position whereat the male end is in the second port, and alignment means on the base and engaged with the operator means to automatically align the male end with the second port when the operator means is moved to the second position.

It is an object of the present invention to provide a sterile means for changing a spike from one peritoneal dialysis bag to another without contamination.

A further object of the present invention is to provide a spike exchanger for C.A.P.D. that can be used with minimal effort by someone who has decreased vision, blindness, decreased manual dexterity or extreme weakness of the hands.

Yet another object of the present invention is to provide a new and improved apparatus for continuous ambulatory peritoneal dialysis.

In addition, it is an object of the present invention to provide a medical apparatus to change a tubular connection from a first bag for holding liquid to a second bag for holding liquid.

Related objects and advantages of the present invention will be apparent from the following description.

DESCRIPTION OF THE PREFERRED EMBODIMENTS

Figure 1:
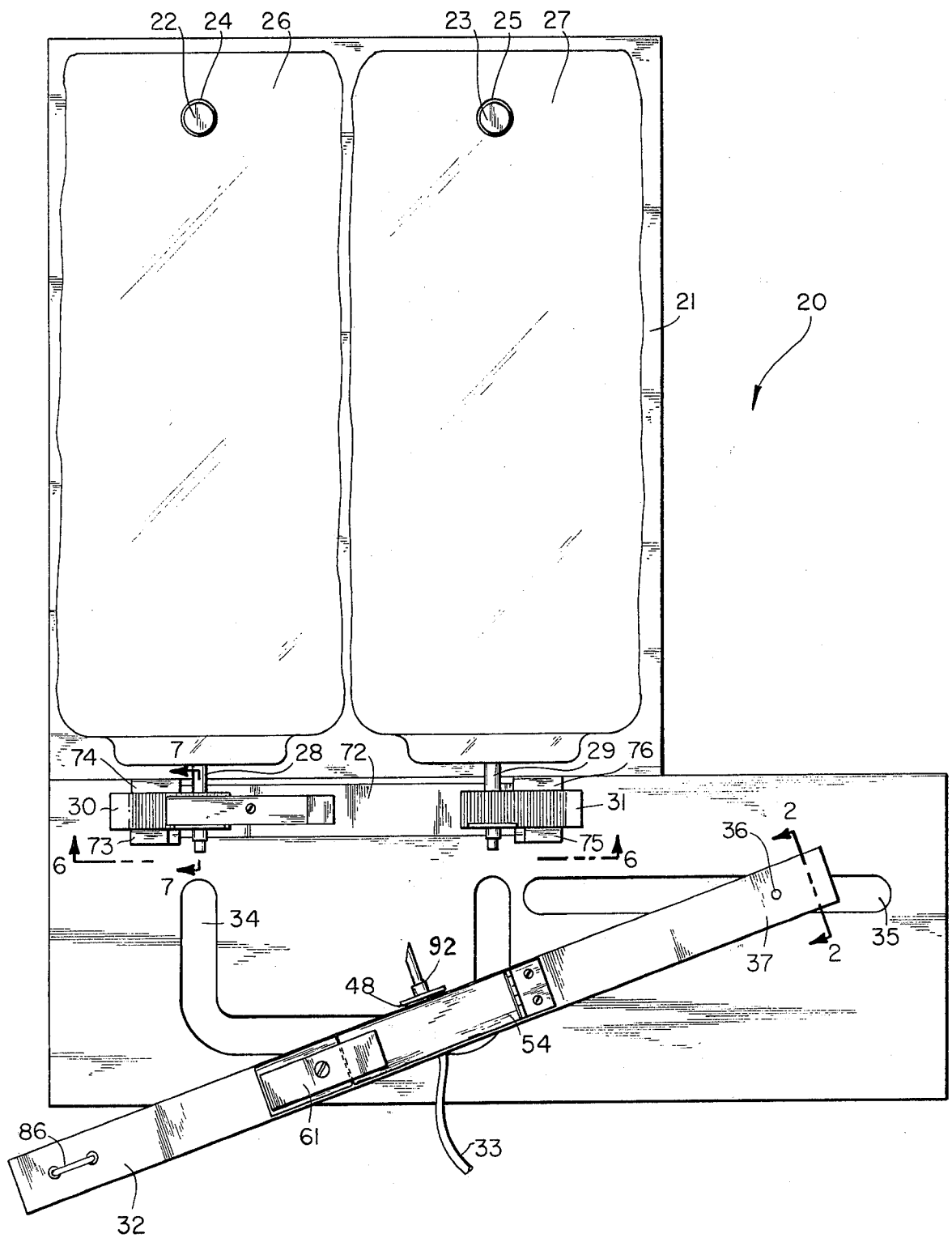
FIG. 1 is a plan view of the preferred embodiment of the spike exchanger incorporating the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown the preferred embodiment of the spike exchanger 20 incorporating the present invention. Spike exchanger 20 includes a base 21 having a pair of pegs 22 and 23 extending cantileveredly upward therefrom. Pegs 22 and 23 are sized to removably fit into a pair of mounting apertures 24 and 25 provided respectively on two commercially available Peritoneal Dialysis bags 26 and 27. Such bags are available, for example, from Artifical Organs Division of Travenol Laboratories, Inc., Deerfield, Ill. 60015. The bags contain Peritoneal Dialysis solution in the amount of 2,000 ml. At the bottom end of each bag is a tubular port 28 and 29 received by a pair of clamps 30 and 31 mounted to base 21.

A slidable and pivotable lever 32 is mounted to base 21 and has means to removably secure and mount spike 92 in turn connected to spike tube 33. A C-shaped slot 34 is formed in base 21 to receive a roller mechanism mounted to lever 32 immediately beneath spike 92. A straight slot 35 is also formed in base 21 and receives a roller mechanism 36 mounted to the proximal end 37 of lever 32. The two legs of slot 34 are aligned with tubes 28 and 29 of bags 26 and 27. Thus, lever 32 may be pivoted about roller mechanism 36 and moved through slots 34 and 35 to move spike 92 toward either tube 28 or 29 to connect the spike to either bag without requiring the patient to manually hold spike 92 during the insertion or removal from either tube 28 or 29.

Figure 2:
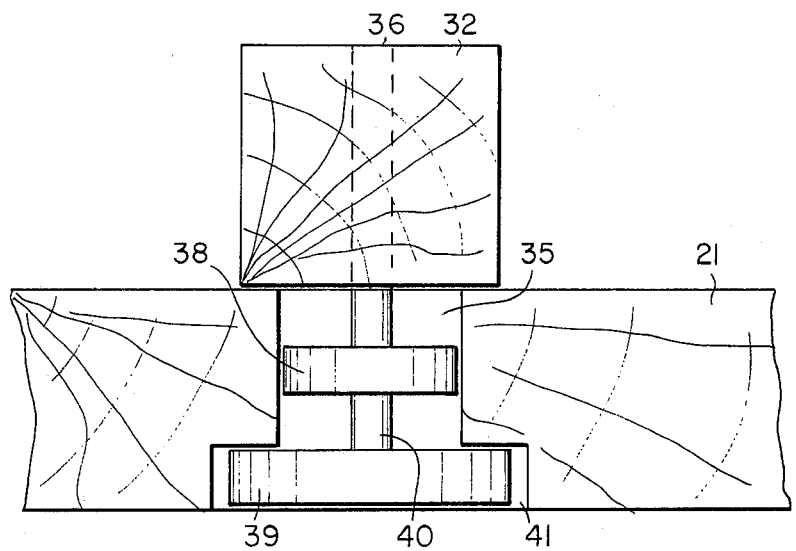
FIG. 2 is an enlarged fragmentary cross-sectional view taken along the line 2—2 of FIG. 1 and view in the direction of the arrows.

One end of lever 32 (FIG. 2) includes a roller mechanism 36 having a first roller 38 and a larger diameter roller 39 rotatably mounted to pin 40 fixedly mounted to lever 32. Roller 38 is slidable the length of slot 35 with a second slot 41 located immediately beneath slot 35 and of larger width to receive roller 39 and prevent the lever from moving upwardly disengaging the base. A similar roller mechanism 42 includes a pair of rollers 43 and 44 received respectively in slots 45 (FIG. 5) and 34 provided in base 21. Roller 43 is larger in diameter than roller 44 and is received in slot 45 located immediately beneath slot 34 and of larger width than slot 34 to prevent lever 32 from moving upwardly disenaging the base. Each roller 43 and 44 are rotatably mounted to pin 46 fixedly mounted to lever 32 with pin 46 being located immediately beneath spike 92.

Figure 3:
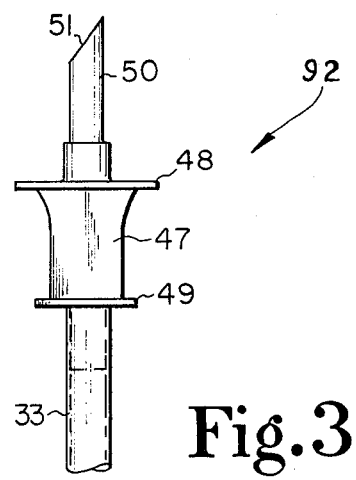
FIG. 3 is an enlarged plan view of the spike and attached tube.
Figure 4:
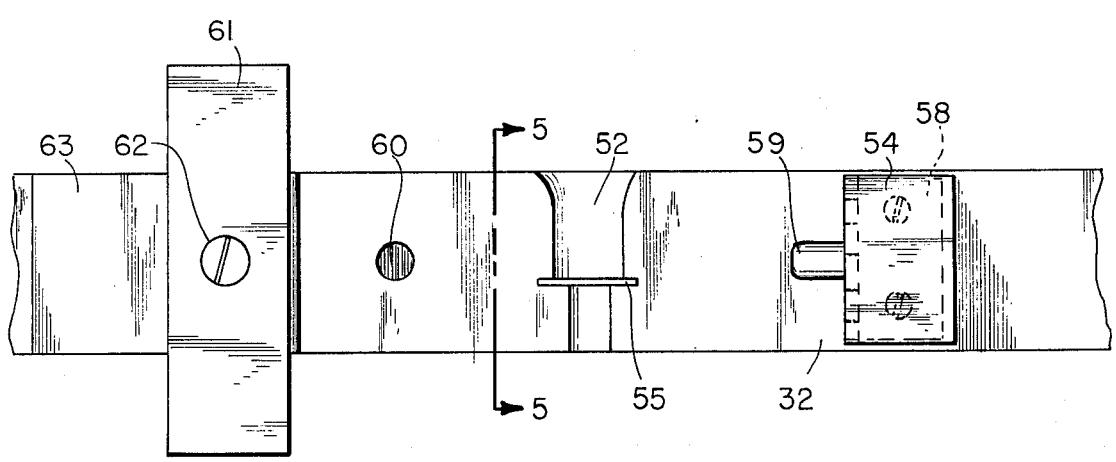
FIG. 4 is an enlarged fragmentary top view of the spike mount shown in the open position.
Figure 5:
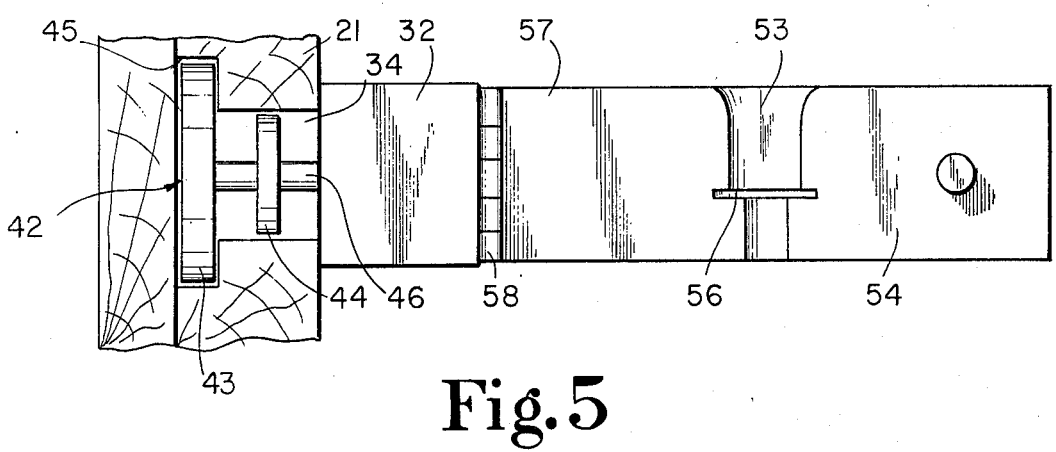
FIG. 5 is a fragmentary cross-sectional view taken along the line 5—5 of FIG. 4 and viewed in the direction of the arrows.

Spike 92 (FIG. 3) includes a main body 47 having a pair of flat plates 48 and 49 mounted to the respective ends of the main body with a passage running through the spike to allow fluid communication between hose 33 and the hollow shank 50 extending outwardly therefrom and terminating at tip 51 for piercing either tube 28 or 29 of bags 26 and 27. A complementary sized recess 52 (FIG. 4) is formed in lever 32 with a similar recess 53 formed in mounting block 54 (FIG. 5). Mounting block 54 is shown in the upward or open position with the spike removed in FIGS. 4 and 5 to illustrate recesses 52 and 53. Recesses 52 and 53 have respectively slots 55 and 56 formed therein to mountingly receive plate 49 (FIG. 3) of the spike. The second plate 48 fits outwardly of block 54 (FIG. 1) when the spike is mounted in recesses 52 and 53 and block 54 is pivoted downward to the closed position. End 57 (FIG. 5) of block 54 is hingedly mounted by a conventional hinge 58 to lever 32. An alignment pin 59 is provided in the distal end of block 54 and is received by aperture 60 in lever 32 when the block is in the downward or closed position. Once mounting block 54 is pivoted to the downward or closed position, a locking member 61 is moved to a position outwardly of and against the distal end of mounting block 54 preventing relative motion between mounting block 54 and lever 32. Locking member 61 is pivotally mounted by a conventional fastener 62 in turn secured to member 63 fixedly mounted to lever 32.

Figure 6:
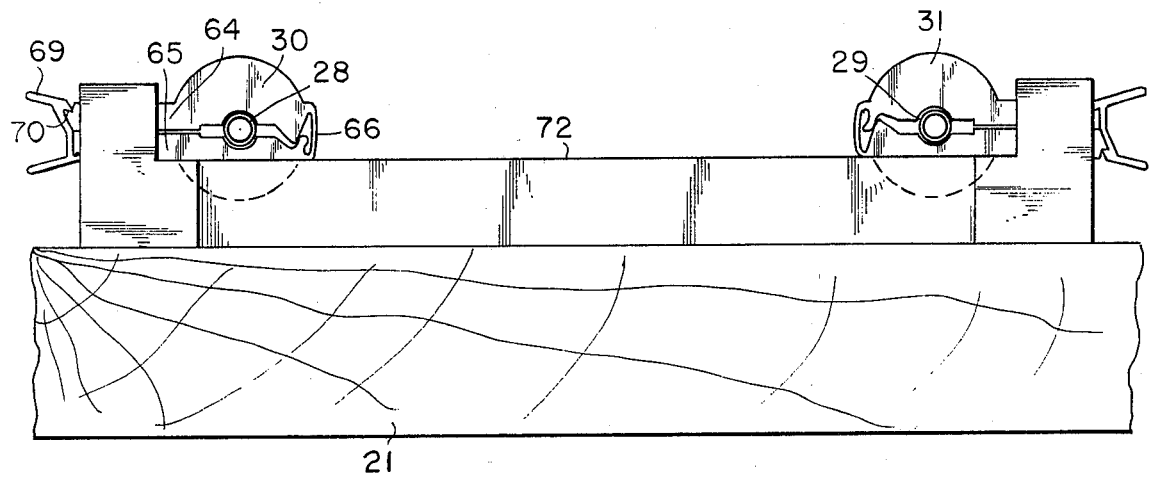
FIG. 6 is an enlarged fragmentary cross-sectional view taken along the line 6—6 of FIG. 1 and viewed in the direction of the arrows.
Figure 7:
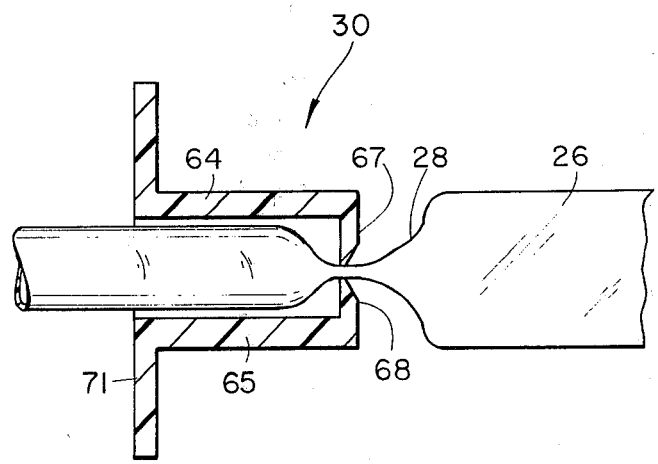
FIG. 7 is an enlarged fragmentary cross-sectional view taken along the line 7—7 of FIG. 1 and viewed in the direction of the arrows.

Tube clamp 30 will now be described it being understood that a similar description applies to tube clamp 31. Clamp 30 (FIG. 6) includes an upper clamp half 64 and a lower clamp half 65 hingedly connected together by means of a plastic hinge 66. Each half portion 64 and 65 have mating ridges 67 and 68 (FIG. 7) which meet and squeeze shut conduit 28 of bag 26 when the top half portion 64 is pivoted to the downward locked position. A bendable locking handle 69 is integrally connected to bottom half portion 65 (FIG. 6) and lockingly and removably engages ridge 70 provided on the distal end of the top half portion 64. To remove conduit 28 from clamp 30, handle 69 may be pivoted downwardly to the left as viewed in FIG. 6 disengaging ridge 70 and allowing top half portion 64 to be pivoted upwardly around hinge 66. The bottom half portion 65 has a semi-circular plate 71 formed thereon which is removably received in a complementary sized slot provided in inlet port holder 72 (FIG. 6). Holder 72 (FIG. 1) consists of an elongated member extending across base 21 and fixedly secured thereto with each end of holder 72 having a pair of ears 73–74 and 75–76 to receive respectively clamps 30 and 31 positioned therebetween. Ears 73 and 74 prevent clamp 30 from moving parallel to base 21; however, clamp 30 along with bag 26 may be picked upwardly and removed from base 21. Ears 75 and 76 likewise prevent motion of clamp 31 in a direction parallel to base 21 with the top half portion of clamp 31 being pivoted upwardly to allow conduit 29 to be removed from the clamp and bag 27 to be removed from base 21. As will be apparent from a later description herein, it is unnecessary to remove clamp 31 from base 21 and as a result, the bottom half portion of clamp 31 is fixedly secured by a bolt or other conventional fastening device to base 21.

Figure 8:
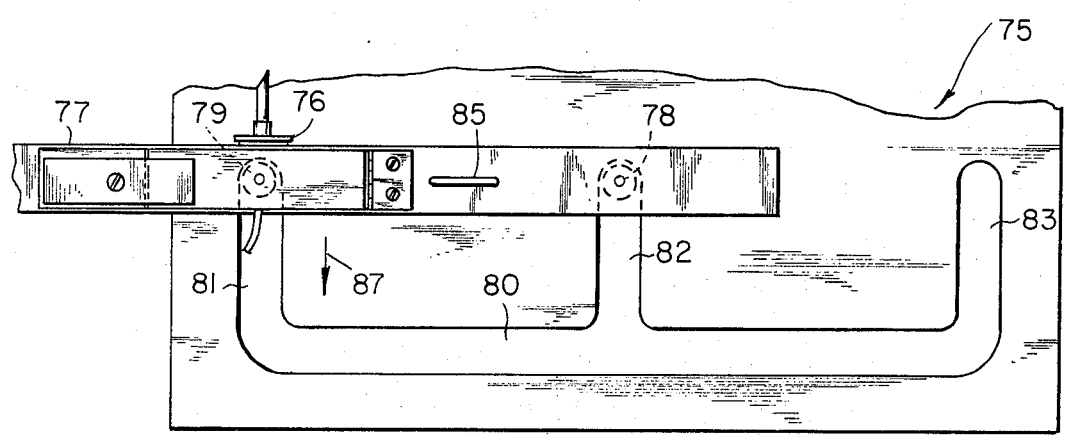
FIG. 8 is a fragmentary plan view of an alternate embodiment of the spike exchanger.

An alternate embodiment of the spike exchanger is partially depicted in FIG. 8. Exchanger 75 is identical to exchanger 20 with the exception of the design of the slot provided in the base for slidably receiving the spike mounting lever. Spike 76 is removably mounted to lever 77 in the same manner as the mounting of spike 92 to lever 32. A roller mechanism 78 identical to roller mechanism 36 is mounted to one end of lever 77 with a second roller mechanism 79 identical to roller mechanism 42 being mounted to lever 77 immediately beneath spike 76. When the spike is engaged with conduit 28 of the left bag 26, roller mechanisms 79 and 78 are positioned respectively in legs 81 and 82 of slot 80 whereas when spike 76 is engaged with conduit 29 of bag 27, roller mechanisms 79 and 78 are positioned respectively in legs 82 and 83 of slot 80. Handle 85 is mounted to lever 77 between roller mechanism 78 and 79 in contrast with the mounting of handle 86 which is positioned at one end of lever 32. The handles may take any form including a peg shape. To remove spike 76 from the left bag 26 and to engage the spike with the right bag 27, handle 85 is grasped and lever 77 is pulled in the direction of arrow 87 and then moved to the right until roller mechanisms 79 and 78 are positioned in legs 82 and 83 of slot 80 with the lever then being pushed in a direction opposite arrow 87. Legs 81 and 82 of the slot are aligned respectively with conduits 28 and 29 of bags 26 and 27.

Figure 9:
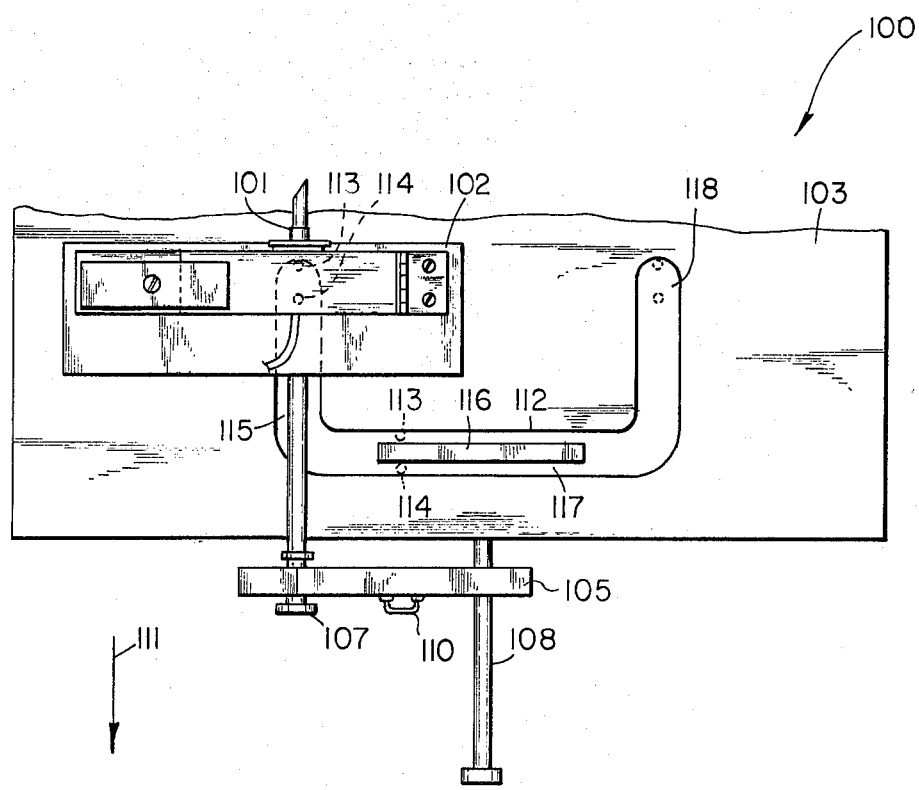
FIG. 9 is a fragmentary plan view of a further embodiment of the spike exchanger.
Figure 10:
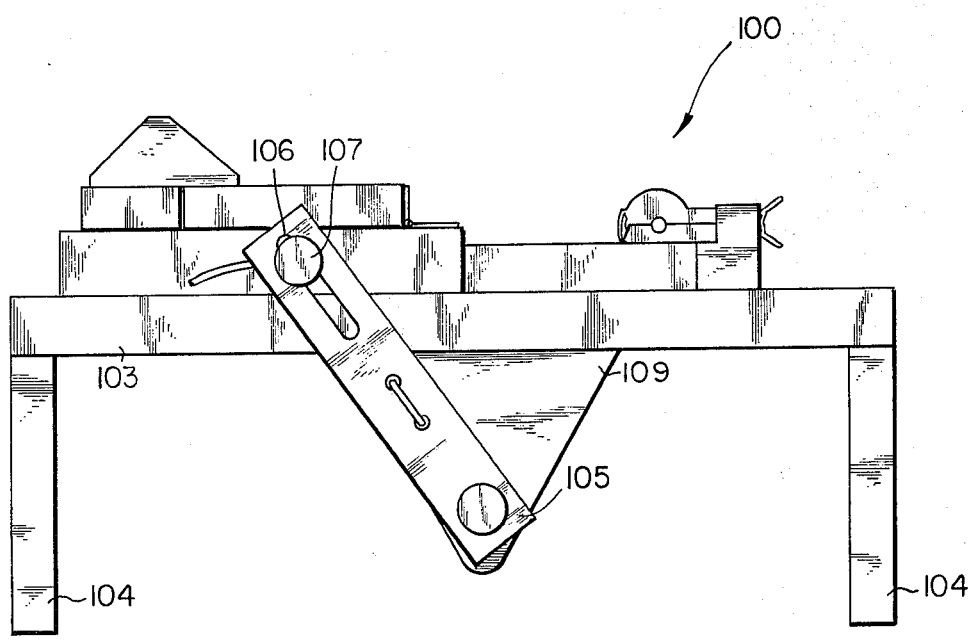
FIG. 10 is an end view of the spike exchanger shown in FIG. 9.

A further embodiment of the spike exchanger is shown in FIGS. 9 and 10. Spike exchanger 100 is identical with spike exchanger 20 with the exception of the design of the slot and the associated mounting lever. Spike 101 is removably mounted to block 102 in a manner identical to the mounting of spike 92 to lever 32. Block 102 is slidably mounted to base 103 which in turn may be supported upon frame 104 (FIG. 10). Pivotally mounted to and beneath base 103 is arm 105 having a slot 106 formed in the top end thereof to slidably receive a double headed rod 107 fixedly mounted to block 102. Arm 105 is slidably mounted to a headed rod 108 fixedly mounted by bracket 109 to base 103. By grasping handle 110 and moving arm 105 in the direction of arrow 111, the arm will pull headed rod 107, block 102 and spike 101 disengaging the spike from the left bag 26. Arm 105 may then be pivoted in a clockwise direction as viewed in FIG. 10 until the spike is aligned with conduit 29 of the right bag 27 with arm 105 then being forced in a reverse direction opposite of arrow 111 until the spike engages conduit 29. Slot 106 is provided to enable rod 107 to move through the slot as arm 105 is pivoted from the left to the right and back. Slot 112 is provided in base 103 and is C-shaped in configuration to slidably receive a pair of roller mechanisms 113 and 114 fixedly mounted to and beneath block 102 with each roller mechanism 113 and 114 being identical in construction to roller mechanism 42. The roller mechanisms are aligned with spike 101 in the direction of leg 115 of slot 112. Thus, when handle 110 is moved to the most outward position in the direction of arrow 111, and the lever pivoted to the right, roller mechanisms 113 and 114 will span on opposite sides ridge 116 extending the length of the portion 117 of slot 112 connecting slot legs 115 and 118 together. Ridge 116 provides for lateral stability as the spike is moved from one bag to another bag. Roller mechanisms 113 and 114 are shown in phantom in portion 117 and slot 118 to illustrate the positioning thereof as spike 101 is moved. Likewise, when the spike is positioned immediately above leg 118 of the slot, the two roller mechanisms will be aligned with conduit 29 in the direction of the length of leg 118. The remaining structure of spike exchanger 100 is identical to that previously described for the other spike exchangers and includes a pair of clamps for removably receiving the bag tubes.

The spike exchanger includes a mechanism to mobilize both the old and new bag of fluid using clamps which are placed over the tubular ports. The spike is placed in a clamp on a moveable portion of the device with the moveable portion then being shifted from the old bag to the new bag, thereby swiftly and sterilely removing the spike from the old bag and placing it in the new bag. To begin, the peritoneal dialysis solution in a first bag is drained into the patient with the empty first bag then being rolled up and carried by the patient. Upon completion of the dwell time, the first empty bag is unrolled with the solution within the patient being allowed to drain back into the first bag. With the embodiment depicted in FIG. 1, the first bag is shown as bag 26. As bag 26 is mounted to base 21, spike exchanger 92 is mounted to lever 32 and clamp 30 is moved to the closed position. Lever 32 is then grasped and pulled outwardly and moved to the right disengaging spike 92 relative to conduit 28. Lever 32 is then moved inwardly to engage spike 92 with conduit 29. Clamp 31 is then opened allowing the contents of bag 27 to drain into the patient. Once bag 27 is empty, the bag may be rolled up along with spike 32 and carried by the patient during the dwell time after which the process is repeated. During the dwell time, bag 26 is emptied and a new bag with fresh peritoneal dialysis solution 15 is mounted to the right side of base 21. The same procedure applies to the embodiment depicted in the other drawings. To ensure a sterile environment between the spike and tube conduit, suitable sterile wrappings, gauze or similar material should be positioned around spike 92 and the mating tubular port 28 or 29 while interconnected. Plate 48 of spike 92 is positioned outwardly and is spaced apart from lever 32 to facilitate the mounting of a clam shaped shell onto the spike with the shell containing therein sterile materials providing a sterile environment.

Pegs 22 and 23 provide mounting means to releasably hold the two bags having tubular ports. Further, clamps 30 and 31 provide a clamp means on base 21 engageable with the pair of tubular ports to releasably limit fluid flow therethrough. Bar 32 along with locking member 54 provide a spike holding and moving means movably mounted to the base and operable to releasably hold spike 92 in fluid communication with tubular port 28 and to move spike 92 away from tubular port 28 to the second tubular port 29. The slots provide a guide means on the base and associated with bar 32 to guide and align the spike with tubular port 29 as the spike is moved thereto. The slot provides a track having a pair of interconnected parallel legs extending away from the tubular ports. The roller mechanisms such as mechanism 42 provide a bearing surface which is slidably moveable over the slot legs to align the spike with the tubular ports. Recesses 52 and 53 provide a recess means to hold in position the spike in line with the tubular ports when the bearing surface is positioned in the respective legs of the slot. Spike 92 is mounted to the end of a patient connectable tube 33 with the spike end fittable into either tubular port 28 or 29. Ears 73–74 and 75–76 along with the slots provided in member 72 receiving the disk shaped bottom half portion 65 of clamp 30 and the disk shaped bottom portion of clamp 31 provide an alignment means to limit relative movement between the clamps and base 21 and further align the tubular ports with the spike.

Many advantages of the present invention will be apparent upon use of the device. Previously, the manual removal of the spike from one bag and manual insertion into the inlet port of a new bag was accomplished with a high risk of contamination. Such risk of contamination is considerably reduced by utilizing the device disclosed herein. Further, my device allows for the procedure to be accomplished by someone who is handicapped with blindness or by someone who is handicapped by having decreased manual dexterity, perhaps secondary to crippling arthritis or muscle weakness. Likewise, the procedure may be accomplished by a patient who is handicapped by being unable to learn the proper manual technique or by someone who is handicapped by having only one upper extremity. The device disclosed herein will decrease the number of episodes of peritonitis and therefore will become very cost effective.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

The invention claimed is:

1. A spike exchanger for continous ambulatory peritoneal dialysis comprising:
   a base having mounting means to releasably hold a first bag with a first port and a second bag with a second port;
   clamp means on said base and engageable with said first port and said second port to releasably limit fluid flow therethrough;
   spike holding and moving means movably mounted to said base and operable to releasably hold a spike in fluid communication with said first port and move said spike away from said first port to said second port; and,
   guide means on said base and associated with said spike holding and moving means to guide and align said spike with said second port as said spike is moved thereto.

2. The spike exchanger of claim 1 wherein:
   said guide means includes a track having a first leg and an interconnected second parallel leg extending away respectively from said first port and said second port;
   said spike holding and moving means includes a bar with a bearing surface slidably moveable over said first leg and said second parallel leg.

3. The spike exchanger of claim 2 wherein said spike holding and moving means includes recess means holding and positioning said spike in line with said first port when said bearing surface is on said first leg and in line with said second port when said bearing surface is on said second leg.

4. The spike exchanger of claim 3 wherein said clamp means includes a first clamp and a second clamp mounted to said base and engageable respectively with said first port and said second port;
   said base includes alignment means receiving said first clamp and said second clamp limiting relative movement therebetween and positioning said first clamp and said second clamp respectively relative to said first leg and said second leg to align said spike with respectively said first port and said second port.

5. The spike exchanger of claim 4 wherein said guide means includes a C-shaped slot in said base and said bar includes at least one depending roller mechanism mounted thereto and extending into said slot.

6. The spike exchanger of claim 5 wherein:
   said recess means is located above said roller mechanism.

7. The spike exchanger of claim 6 wherein said bar includes a second roller mechanism mounted at one end thereof slidably mounted to said base with said bar pivotable about said second roller mechanism to move said spike from said first leg into said second leg.

8. The spike exchanger of claim 7 wherein said spike holding and moving means includes a locking member pivotally mounted to said bar and having a second recess aligned with said recess means to releasably hold said spike.

9. The spike exchanger of claim 6 wherein:
   said bar includes a second depending roller mechanism mounted adjacent said one depending roller mechanism;
   said base includes a stabilizer rib positioned in said slot between said first and second legs and positioned between each roller mechanism as said bar moves from said first leg to said second leg.

10. The spike exchanger of claim 9 and further comprising a control member with a first end portion and a second end portion, said first end portion being pivotally mounted to said base and said second end portion slidably mounted to said bar, said control member pivotable to move said spike from said first port to said second port.

11. The spike exchanger of claim 4 wherein said guide means includes an E-shaped slot in said base and said bar includes a pair of depending roller mechanisms mounted thereto and extending into said slot.

12. A medical apparatus comprising:
   a first bag for holding liquid and including a first tubular port;
   a second bag for holding liquid and including a second tubular port;
   a frame with mounting means to releasably hold said first bag and said second bag;
   clamp means mounted to said frame and releasably engaged with said first tubular port and said second tubular port to control fluid flow therethrough;
   a patient connectable tube with a spike shaped male end in fluid communication with and fittable into said first tubular port when aligned therewith and into said second tubular port when aligned therewith;

operator means movably mounted to said base and releasably holding said spike shaped male end, said operator means movable from a first position whereat said male end is in said first port to said second position whereat said male end is in said second port; and, alignment means on said base and engaged with said operator means to align said male end with said second port when said operator means is moved to said second position.

13. The medical apparatus of claim 12 wherein: said operator means includes a member slidably mounted to said base;

said alignment means includes a track with interconnected parallel legs extending away from said first tubular port and said second tubular port.

14. The medical apparatus of claim 13 wherein: said operator means and said alignment means include an intercooperating slot arrangement and roller mechanism slidably guiding said spike shaped male end to said first tubular port and said second tubular port.

* * * * *